United States Patent [19]

Schenker et al.

[11] Patent Number: 4,931,218

[45] Date of Patent: Jun. 5, 1990

[54] SULFATED HYDROXY MIXED ETHERS, A PROCESS FOR THEIR PRODUCTION, AND THEIR USE

[75] Inventors: Gilbert Schenker, Erkrath; Robert Piorr, Duesseldorf; Sabine Luettge, Moenchen-Gladbach, all of Fed. Rep. of Germany

[73] Assignee: Henkel Kommanditgesellschaft auf Aktien, Duesseldorf, Fed. Rep. of Germany

[21] Appl. No.: 218,719

[22] Filed: Jul. 13, 1988

[30] Foreign Application Priority Data

Jul. 15, 1987 [DE] Fed. Rep. of Germany ....... 3723354

[51] Int. Cl.$^5$ .................... C11D 1/29; C11D 1/37; C11D 11/04

[52] U.S. Cl. .................... 252/551; 252/174.21; 252/174.22; 252/550; 252/DIG. 5; 252/DIG. 6

[58] Field of Search ............... 252/531, 532, 550, 551; 558/34

[56] References Cited

U.S. PATENT DOCUMENTS

| | | | |
|---|---|---|---|
| 3,931,057 | 1/1976 | Liu | 252/551 |
| 3,936,317 | 2/1976 | Lehmann et al. | 134/29 |
| 4,592,875 | 6/1986 | Kesling, Jr. et al. | 252/551 |
| 4,600,523 | 7/1986 | Piorr et al. | 252/174.22 |

FOREIGN PATENT DOCUMENTS 0913001 12/1962 United Kingdom .
1089882 11/1967 United Kingdom .

OTHER PUBLICATIONS

In re Durefen, Jr. et al., 226, USPQ 359–362.

*Primary Examiner*—Paul Lieberman
*Assistant Examiner*—A. Beadles-Hay
*Attorney, Agent, or Firm*—Ernest G. Szoke; Wayne C. Jaeschke; Henry E. Millson, Jr.

[57] ABSTRACT

Sulfated hydroxyalkyl polyethylene glycol and hydroxyalkyl polypropylene glycol ethers corresponding to general formula (II)

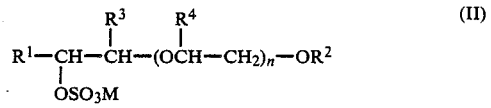

in which $R^1$ is hydrogen or a linear $C_1$–$C_{16}$ alkyl radical,
$R^2$ is a linear or branched, saturated $C_1$–$C_{22}$ alkyl radical,
$R_3$ is hydrogen or a linear $C_1$–$C_{16}$ alkyl radical,
$R^4$ is hydrogen or a methyl group,
M represents hydrogen, ammonium, alkylammonium, alkanolammonium, in which the alkyl and alkanol radicals each contain from 1 to 4 carbon atoms, or a monovalent metal atom, and
n is a number of 1 to 30,
with the proviso that the total number of carbon atoms in $R^1$ and $R_3$ is between 6 and 16, and mixtures of such compounds; a process for the preparation of the compounds of formula (II) from the corresponding hydroxyalkyl polyethylene glycol and hydroxyalkyl polypropylene glycol ethers by reaction with gaseous sulfur trioxide or chlorosulfonic acid at an elevated temperature; and the use of the sulfated compounds or mixture thereof as wetting agents and raw materials for detergents and cleaning preparations, especially cosmetic compositions.

39 Claims, No Drawings

SULFATED HYDROXY MIXED ETHERS, A PROCESS FOR THEIR PRODUCTION, AND THEIR USE

BACKGROUND OF THE INVENTION

1. Field of the Invention

This invention relates to sulfated hydroxyalkyl polyethylene and hydroxyalkyl polypropylene glycol ethers and mixtures thereof, to a process for the production of these compounds and mixtures thereof, and to their use as wetting agents and raw materials for detergent compositions.

2. Statement of Related Art

Hydroxyalkyl polyethylene glycol and hydroxyalkyl polypropylene glycol ethers corresponding to general formula (I)

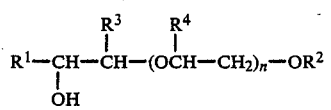
(I)

are known from the prior art. Thus, U.S. Pat. No. 4,600,523 describes compounds corresponding to general formula (I), in which $R^1$ is a linear $C_6$–$C_{16}$ alkyl radical,
$R^2$ is a linear or branched $C_4$–$C_8$ alkyl radical,
$R^3$ is hydrogen or a $C_1$–$C_8$ alkyl radical,
$R^4$ is hydrogen and
n has a value of 7 to 12,
with the proviso that the total number of carbon atoms in $R^1$ and $R^3$ is between 6 and 16,
and the use of these compounds as foam inhibitors for low-foam cleaning preparations.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that hydroxylakyl polyethylene glycol and hydroxyalkyl polypropylene glycol ethers corresponding to formula (I) can be sulfated with good results to give sulfated hydroxy mixed ethers which not only are eminently suitable for use as low-foam wetting agents and raw materials for detergents (detergent compositions), but are also safe and satisfy most current government requirements with respect to their toxicity. The compounds of the invention are also biodegradable, so that there are no ecological objections to their use.

The present invention relates to sulfated hydroxyalkyl polyethylene glycol and hydroxyalkyl polypropylene glycol ethers corresponding to general formula (II).

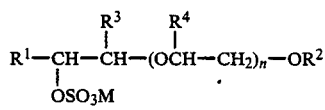
(II)

in which
$R^1$ is hydrogen or a linear $C_1$–$C_{16}$ alkyl radical,
$R^2$ is a linear or branched, saturated $C_1$–$C_{22}$ alkyl radical,
$R^3$ is hydrogen or a linear $C_1$–$C_{16}$ alkyl radical,
$R^4$ is hydrogen or a methyl group,
M represents hydrogen, ammonium, alkylammonium, alkanolammonium, in which the alkyl and alkanol radicals each contain from 1 to 4 carbon atoms, or a monovalent metal atom, and
n has a value of from 1 to 30,
with the proviso that the total number of carbon atoms in $R^1$ and $R^3$ is between 6 and 16,
and to mixtures of two or more such compounds.

The present invention also relates to a process for the production of sulfated hydroxyalkyl polyethylene glycol and hydroxyalkyl polypropylene glycol ethers of formula II or mixtures thereof wherein epoxides corresponding to general formula (III)

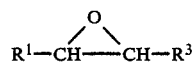
(III)

in which
$R^1$ and $R^3$ are as defined above,
are reacted with alcohol alkoxylates corresponding to general formula (IV)

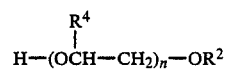
(IV)

in which
$R^2$, $R^4$, and n are defined above,
at an elevated temperature in the presence of a catalyst to form hydroxyalkyl polyethylene glycol and hydroxyalkyl polypropylene glycol ethers corresponding to general formula (I)

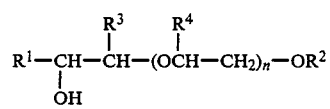
(I)

in which
$R^1$, $R^2$, $R^3$, $R^4$, and n are defined above,
or mixtures thereof, the resulting compounds (I) or their mixtures are reacted at a temperature in the range of 10° to 40° C. with a sulfating agent, the crude solfonation product is introduced into an aqueous basic solution, and the mixture is kept at an elevated temperature, with subsequent adjustment to a pH value in the neutral or mildly alkaline range and, if desired, the products (II) thus obtained or their mixtures are isolated from the reaction mixture by methods known per se.

The present invention also relates to the use of the sulfated hydroxyalkyl polyethylene glycol and hydroxyalkyl polypropylene glycol ethers of formula (II) or mixtures thereof as wetting agents and as raw materials for detergents.

In general formula (II) above, $R^1$ is hydrogen or a linear $C_1$–$C_{16}$ alkyl radical. Accordingly, suitable substituents other than hydrogen for $R^1$ include the radicals methyl, ethyl, n-propyl, n-butyl, n-pentyl, n-hexyl, n-heptyl, n-nonyl, n-decyl, n-undecyl, n-dodecyl, n-tridecyl, n-tetradecyl, n-pentadecyl, and n-hexadecyl.

$R^3$ in general formula (II) above is hydrogen or a linear $C_1$–$C_{16}$ alkyl radical. In addition to hydrogen, therefore, $R^3$ can represent the alkyl radicals given above for $R^1$.

In preferred hydroxyalkyl polyethylene glycol and hydroxyalkyl polypropylene glycol ethers of formula (II), $R^1$ represents linear $C_8$–$C_{12}$ alkyl radicals and $R^3$ is hydrogen.

According to the invention, $R^2$ in formula (II) above is a linear or branched, saturated $C_1$–$C_{22}$ alkyl radical. Accordingly, suitable substituents $R^2$ include methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, and n-docosyl radicals, and also the branched-chain isomers of these alkyl radicals.

In a preferred embodiment, $R^2$ represents a linear, saturated $C_1$–$C_{22}$ alkyl radical.

One particularly preferred embodiment comprises sulfated hydroxyalkyl polyethylene glycol and hydroxyalkyl polypropylene glycol ethers of formula (II), in which $R^2$ is a linear, saturated $C_1$–$C_{12}$ alkyl radical.

In formula (II) above, $R^4$ is hydrogen or a methyl group, preferably hydrogen.

In formula (II), n has a value of 1 to 30, and preferably a value of 1 to 12. This means that, in the hydroxyalkyl polyethylene glycol and hydroxyalkyl polypropylene glycol ethers according to the invention, 1 to 30 ethoxy or propoxy groups and preferably 1 to 12 ethoxy or propoxy groups are incorporated in the molecular chain. However, in these compounds, ethoxy groups and propoxy groups can also be incorporated in the molecular chain in any ratio and in any sequence. Mixed ethers such as these also fall within the scope of formula (II).

In formula (II), M is hydrogen, ammonium, alkylammonium, alkanolammonium or a monovalent metal ion, the alkyl and alkanol radicals of the organic ammonium ions each containing from 1 to 4 carbon atoms. In compounds of general formula (II) which are preferred in accordance with the invention, M is an alkali metal; compounds (II) in which M is Sodium or potassium being particularly preferred.

One advantage of the compounds of the invention over other wetting agents and detergent raw materials used in the prior art is that they do not foam, and in addition show comparable, if not better, wetting power than most of the prior art compounds.

However, the compounds of formula (II) also show outstanding biodegradability, which was one of the primary objectives of the present invention. Even in the CB (closed bottle) test, which imposes far more stringent demands than other standard test methods on the biodegradability of the tested compounds, very good results were obtained: the compounds show $BOD_{30}$ values of, in some cases, distinctly above 60%. The compounds of the invention thus satisfy current legal requirements. Accordingly, there is no danger of wastewater pollution where the compounds of formula (II) are employed.

The present invention also encompasses mixtures of two or more compounds of formula (II), which can be obtained by the process described above. Mixtures of several compounds (II) are formed in particular when intermediates accumulate in the course of an industrial process in the form of mixtures of several compounds of the same kind. In general, the further treatment of mixtures such as these does not produce a single reaction product, but instead product mixtures although the constituents of these mixtures do show homologous structures and differ only marginally in their properties.

For example, the present invention encompasses mixtures of compounds (II) which differ in their degree of ethoxylation or propoxylation, i.e. in which n in formula (II) is scattered over a more or less wide range.

Accordingly, starting materials for the process for preparing the compounds of formula (II) include epoxides of formula (III) above. Epoxides such as these are formed from olefins obtainable petrochemically in large quantities, in the majority of cases monoolefins, by know epoxidation reactions, for example by reaction of the olefins with percarboxylic acids or similar epoxideforming reagents. Epoxides (III) in the context of the invention can be 1,2-epoxides. In terminal epoxides such as these, which are preferred in accordance with the invention, $R^3$ is hydrogen and $R^1$ in formula (III) above is a linear $C_1$–$C_{16}$ alkyl radical, preferably a $C_6$–$C_{16}$, and more preferably a $C_8$–$C_{12}$ alkyl radical. However, epoxides containing non-terminal oxirane rings can also be used herein.

Reactants for the above-described epoxides of formula (III) are alcohol alkoxylates of formula (IV). The compounds (IV) are formed in known manner from alcohols and olefin epoxides. In the present case, alcohol alkoxylates of formula (IV) are compounds formed from the corresponding alcohols and ethylene oxide or propylene oxide. Preferred reactants in the present process are alcohol alkoxylates of formula (IV) in which $R^2$ is a linear, saturated $C_1$–$C_{22}$ alkyl radical. Examples of these alkyl radicals for this meaning of $R^2$ are given above for the compounds of formula (II). $R^2$ is more preferably a linear, saturated $C_1$–$C_{12}$ alkyl radical, and most preferably a $C_1$–$C_4$ alkyl radical. According to the invention, this means that, for the preparation of the educts for the production of the alcohol alkoxylates of formula (IV) to be used in accordance with the invention, it is most preferred to react $C_1$–$C_4$ alcohols with alkylene oxides, such as ethylene oxide or propylene oxide. In the present case, therefore, such alcohols are alcohols from the group methanol, ethanol, n-propanol and n-butanol. In this preferred embodiment, alcohols from this group are reacted with ethylene oxide or propylene oxide, in which instance the particularly preferred alcohol alkoxylates of formula (IV) are formed. In this case, the reaction products with ethylene oxide are preferred so that, in the alcohol alkoxylates (IV) suitable for use in accordance with the invention, $R^4$ is preferably hydrogen. The reaction ratio, which also ultimately determines the number of alkoxy groups in the molecule of the compounds corresponding to general formula (IV), is in the range of from 1:1 to 1:30, so that the numerical average for n is a value in the range of from 1 to 30, and preferably a value in the range of from 1 to 12.

Alcohol alkoxylates, in which the recurring unit consists of ethoxy and propoxy groups in any ratio and in any sequence in the chain, are also suitable for use in the present process provided the number n for the recurring units is in the above-mentioned range.

In the process of the invention for the preparation of the compounds of formula (II), a molar ratio of approximately 1:1 is adjusted in the reaction of (III) with (IV).

This reaction is carried out at an elevated temperature. Accordingly, this means that the reaction mixture is heated—where appropriate in an inert gas atmosphere—to a reaction temperature in the range of 100° to 180° C., at which the reaction then takes place at an adequate velocity and with a satisfactory yield. A reaction temperature in the range of from 120° to 160° C. is preferred.

The process for the preparation of the hydroxyalkyl polyethylene glycol and hydroxyalkyl polypropylene glycol ethers of formula (I) is carried out in the presence of a catalyst. A quantity of catalyst of from 0.01 to 2.0% by weight, based on the total weight of the reaction mixture, is sufficient for carrying out the reaction. According to the invention, both acidic and basic catalysts can be used. Preferred catalyst systems include alkali metal alcoholates, mineral acids, such as $H_2SO_4$, or Lewis acids, such as $BF_3$ etherate. The preferred catalyst for the process according to the invention is sodium methylate.

The first step of the process of the invention is illustrated by the following reaction scheme:

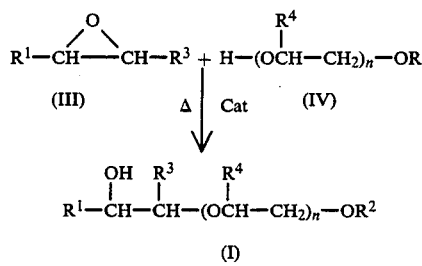

As discussed above, not only individual compounds corresponding to general formula (I), but also mixtures of such compounds are formed in the first step of the process of the invention in accordance with the above reaction scheme. This results on the one hand from the fact that, in certain cases, the oxirane ring of the epoxide used can be opened in two different directions so that different products can be formed and, on the other hand, also from the fact that product mixtures can be used as educts. Thus, the reaction of the alcohols with alkylene oxides in certain molar ratios does not give an individual compound, but instead mixtures of various compounds (IV) with a more or less wide distribution of the number of alkoxy groups in the molecule, i.e. with a more or less wide range for n in general formula (IV). The use of mixtures of the alcohol alkoxylates (IV) in the process of the invention must of course also result in a mixture of compounds (I). Mixtures such as these and processes for their production are also covered by the present invention.

The second step of the process of the invention comprises reacting the compounds (I) obtained in the first step or mixtures thereof with a sulfating agent. This reaction takes place at a temperature in the range of from 10° to 40° C., depending on the sulfating agent used.

A number of compounds can be used as sulfating agents in the process of the invention. Chlorosulfonic acid or, in a particularly preferred embodiment, gaseous sulfur trioxide are used with particular advantage. Gaseous $SO_3$ is introduced into the reaction system containing the compound (I) or mixtures thereof, for example by driving it out from oleum, i.e. superconcentrated sulfuric acid or sulfuric acid enriched with $SO_3$, for example using a submerged pipe. It is preferred to react compound (I) with the sulfating agent in a molar ratio of from 1:1.05 to 1:1.1.

In one preferred embodiment of the process of the invention, the reaction is controlled by diluting the gaseous sulfur trioxide used as sulfating agent with gases that are inert under the reaction conditions. Above all, this facilitates control of the reaction temperature.

Air or nitrogen can advantageously be used as the gas inert under reaction conditions. The proportion of $SO_3$ in the air or nitrogen is preferably in the range of from 1 to 10% by volume. Temperature control in the range of from 10° to 40° C. can readily be achieved in this way.

The second step of the process of the invention as described above is illustrated by the following reaction scheme:

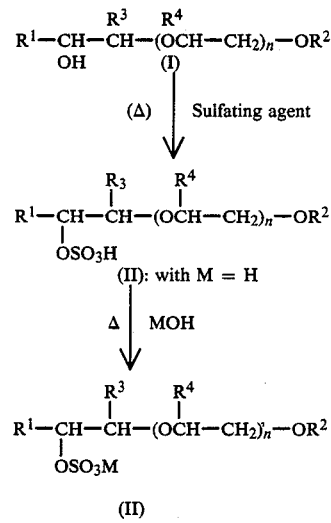

In the process of the invention, the crude sulfonation product is subsequently introduced into an aqueous, basic solution and the resulting mixture maintained at an elevated temperature. In one preferred embodiment, the aqueous basic solution used is a solution containing alkali metal hydroxides, ammonia, one or more alkylamines containing 1 to 4 carbon atoms per alkyl group, or one or more alkanolamines containing 1 to 4 carbon atoms per alkanol group, into which the crude sulfonation product is gradually introduced. Examples of alkylamines include methylamine, ethylamine, n-propylamine, isopropylamine, n-butylamine, and the corresponding di- and tri- alkylamines. Examples of alkanolamines include mono-, di-, and tri-ethanol, propanol and butanol amines. Aqueous sodium hydroxide or potassium hydroxide or a solution containing ammonia, one or more $C_1$ and/or $C_2$ alkylamines and/or one or more $C_2$ and/or $C_3$ alkanolamines as basic components is used with particular advantage. Where ammoniacal or amine-containing basic solutions are used, a metal atom in general formula (II) is replaced by the corresponding ammonium group. Where aqueous solutions containing alkali metal hydroxides, more especially NaOH or KOH, are used, as is preferably the case in accordance with the invention, the concentration of alkali metal hydroxide is selected to be in the range from 1.0 to 1.3 mol alkali metal hydroxide per mol of added $SO_3$. This concentration of alkali metal hydroxide in the solution initially introduced has the advantage that not only is the acidic sulfonation product completely converted into the corresponding alkali metal salt, but pH adjustment in the following step of the process requires only a limited addition of acid.

After introduction of the crude sulfonation product into the aqueous basic solution, the reaction mixture is kept for a while at an elevated temperature. This temperature is preferably in the range of from 60° to 100° C., a temperature of approximately 95° C. maintained for a period of approximately 30 minutes having proved successful in practice.

Before the products of general formula (II) obtained in this way are further used, the reaction mixture is adjusted to a pH value in the neutral or mildly alkaline range.

In the most simple case, this is done by neutralizing the reaction mixture obtained in the process step described above with dilute mineral acids, for example with dilute sulfuric acid. If desired, the resulting products (II) or a mixture of several such compounds can then be isolated from the reaction mixture.

Apart from the formation of new and—in relation to the prior art—improved products (II), the process of the invention has the major advantage over state-of-the-art processes that the compounds corresponding to general formula (II) can be prepared on an industrial scale from educts readily obtainable in high yields. High degrees of sulfation are achieved and the desired compounds are formed in high quality and in high purity, disregarding the formation of product mixtures which in no way limit the usefulness of the compounds (II) obtained.

The compounds of formula (II) obtainable as described above or the mixtures of such compounds obtained by the process of the invention are used as wetting agents and as raw materials for detergent compositions. For this particular application, the compounds (II) obtained have the advantage that they are low-foaming.

In addition, the compounds of formula (II) are completely biodegradable. By virtue of the linear terminal groups, they lend themselves to microbial degradation in a relatively short time and pose no threat of long-term pollution of the water. Accordingly, wastewaters containing such compounds do not pollute the environment.

The sulfated hydroxy mixed ethers of formula (II) also show satisfactory compatibility with the skin and mucous membrane. Accordingly, they are also suitable as raw materials for cosmetic washing and cleaning preparations. They are highly compatible with other, high-foaming surfactants of the type typically used in the cosmetics field, for example fatty alcohol sulfates and fatty alcohol polyglycol ether sulfates. Such mixtures of sulfated hydroxy mixed ethers according to the invention and fatty alcohol sulfates or fatty alcohol polyglycol ether sulfates based on linear $C_{12}$-$C_{18}$ fatty alcohols or adducts of 1 to 12 mol ethylene oxide with such fatty alcohols are suitable, for example, as raw materials for the production of liquid soaps, shampoos, shower and bath preparations. It was found, in particular, that aqueous solutions of mixtures of the sulfated hydroxyalkyl polyethylene glycol and hydroxyalkyl polypropylene glycol ethers of formula (II) of the invention and fatty alcohol sulfates and/or fatty alcohol polyglycol ether sulfates show a particularly advantageous foam performance. The foam developed by such mixtures proved to be much more stable against the influence of calcium soap loads than the individual components of the mixtures used alone. This is of particular advantage for soap-containing compositions or for compositions to be used in hard water in conjunction with soap without impairing the foam. Examples of such compositions are foam bath additives whose foam should be stable in hard water, even when fatty acid soap is to be employed.

The fatty alcohol sulfates and fatty alcohol polyglycol ether sulfates which show especially pronounced foam stability in mixtures with the sulfated hydroxyalkyl polyethylene glycol and hydroxyalkyl polypropylene glycol ethers of formula (II) of the invention include those of formula (V)

$$R^5-(O-CH_2-CH_2)_x-OSO_3A \qquad (V)$$

in which $R^5$ is a linear or branched $C_{10}$-$C_{16}$ alkyl radical,

X is a number of from 0 to 10, and

A represents ammonium ion, a mono-, di- or trialkanolammonium ion having from 2 to 4 carbon atoms in the alkanol radicals, an alkali metal ion, or a magnesium ion equivalent.

$R^5$ is preferably a linear primary $C_{12}$-$C_{14}$ alkyl radical.

In these mixtures the weight ratio of sulfated hydroxy mixed ethers (II) to fatty alcohol (polyglycol) ether sulfates (V) is in the range of from 10:90 to 90:10, and preferably in the range of from 10:90 to 50:50.

The invention is illustrated but not limited by the following Examples where the following abbreviations are used:

WAS=washing-active substance (sulfonate and sulfate component);

AS=active substance (dry residue minus inorganic salts and unsulfated fractions);

US=unsulfonated component;

DS=degree of sulfonation;

DR=dry residue.

EXAMPLES

EXAMPLE 1

A reaction product of 1 mol of 1,2-epoxyoctane and 1 mol of the adduct of 10 mol of ethylene oxide with 1 mol of n-butanol was used as starting material.

23.7 g (0.296 mol) gaseous sulfur trioxide (driven put from 36.4 g oleum) were introduced over a period of 15 minutes through a submerged pipe into a standing laboratory reactor which was filled with 162.6 g (0.282 mol) of the starting material and heated to 35° C. The reaction mixture was neutralized with 24.8 g (0.311 mol) of a 50% of weight aqueous solution of sodium hydroxide and then stirred for 30 minutes at 95° C. Finally, a pH of 7.5 was adjusted with dilute sulfuric acid and the indicator used (phenolphthalein) destroyed with 1 ml of a 13% by weight aqueous sodium hypochlorite solution.

The following analytical data were determined:

DS 85.6% by weight
DR 33.4% by weight
AS 31.1% by weight
WAS 26.6% by weight
US 3.8% by weight
NaCl 0.07% by weight
Na$_2$SO$_4$ 2.2% by weight

EXAMPLE 2

A reaction product of 1 mol 1,2-epoxytetradecane and 1 mol of the adduct of 10 mol ethylene oxide with 1 mol n-butanol was used as the starting material.

286.5 g (0.5 mol) of the starting material were introduced into a flask with plane joints. 61.2 g (0.525 mol)

chlorosulfonic acid were introduced over a period of 20 minutes in a gentle stream of argon through a dropping funnel with pressure equalization and extended dropping spout (submerged pipe), the temperature not exceeding 30° C. The reaction mixture was neutralized with 44.1 g of a 50% by weight aqueous solution of sodium hydroxide and made up to 750 g of paste. The following analytical data were determined:
DS 96.1% by weight
DR 48.9% by weight
AS 47.6% by weight
WAS 46.2% by weight
$Na_2SO_4$ 1.3% by weight

EXAMPLES 3 to 68

Other compounds corresponding to general formula (II) characterized in Table 1 below were prepared by the method described in Examples 1 and 2.

In Table 1 the alkyl radicals $R^1$ and $R^2$ are only identified by the number of their carbon atoms. It is understood that e.g. $C_1$ indicates a $CH_3$ radical. $C_{12}$ indicates a $C_{12}H_{25}$ radical etc.

TABLE 1

Examples 3–68: Compounds prepared corresponding to general formula (II) ($R^3$ = H)

| Example | $R^1$ | $R^2$ | $R^4$ | n | M | DS % | DR % | AS % | US % | WAS % |
|---|---|---|---|---|---|---|---|---|---|---|
| 3 | $C_{10}$ | $C_1$ | H | 1 | Na | 95,5 | 46,2 | 42,4 | 1,1 | 37,2 |
| 4 | $C_{12}$ | $C_1$ | H | 1 | Na | 87,3 | 36,5 | 31,8 | 3,0 | 27,8 |
| 5 | $C_6$ | $C_1$ | H | 2 | Na | 97,1 | 64,3 | 61,6 | 1,1 | 52,5 |
| 6 | $C_8$ | $C_1$ | H | 2 | Na | 96,7 | 53,7 | 51,5 | 1,0 | 42,5 |
| 7 | $C_{10}$ | $C_1$ | H | 2 | Na | 97,1 | 43,9 | 42,2 | 0,8 | 36,3 |
| 8 | $C_{12}$ | $C_1$ | H | 2 | Na | 93,3 | 36,7 | 34,9 | 1,6 | 29,1 |
| 9 | $C_{14}$ | $C_1$ | H | 2 | Na | 85,0 | 51,3 | 47,5 | 5,6 | 40,4 |
| 10 | $C_{16}$ | $C_1$ | H | 2 | Na | 89,5 | 43,2 | 39,8 | 3,5 | 36,7 |
| 11 | $C_6$ | $C_1$ | H | 4 | Na | 97,3 | 68,1 | 66,6 | 1,4 | 60,2 |
| 12 | $C_8$ | $C_1$ | H | 4 | Na | 96,3 | 65,0 | 62,4 | 1,5 | 50,6 |
| 13 | $C_{14}$ | $C_1$ | H | 4 | Na | 86,0 | 58,2 | 56,1 | 6,4 | 47,8 |
| 14 | $C_{16}$ | $C_1$ | H | 4 | Na | 77,8 | 68,2 | 65,5 | 13,9 | 58,6 |
| 15 | $C_{10}$ | $C_1$ | H | 5 | Na | 98,1 | 46,7 | 45,0 | 0,6 | 38,1 |
| 16 | $C_{12}$ | $C_1$ | H | 5 | Na | 96,0 | 53,7 | 52,0 | 1,5 | 44,0 |
| 17 | $C_6$ | $C_1$ | H | 10 | Na | 95,7 | 50,3 | 49,2 | 1,6 | 42,1 |
| 18 | $C_{10}$ | $C_1$ | H | 10 | Na | 95,8 | 53,9 | 53,0 | 1,7 | 45,8 |
| 19 | $C_{14}$ | $C_1$ | H | 10 | Na | 94,8 | 48,2 | 47,0 | 2,1 | 44,2 |
| 20 | $C_8$ | $C_1$ | H | 11 | Na | 86,3 | 77,0 | 71,1 | 8,7 | 63,9 |
| 21 | $C_{12}$ | $C_1$ | H | 11 | Na | 89,8 | 77,6 | 75,0 | 6,6 | 66,4 |
| 22 | $C_{16}$ | $C_1$ | H | 11 | Na | 88,9 | 51,2 | 49,1 | 5,4 | 45,1 |
| 23 | $C_2$ | $C_4$ | H | 1 | Na | 81,0 | 41,7 | 39,4 | 6,1 | 33,5 |
| 24 | $C_6$ | $C_4$ | H | 1 | Na | 96,9 | 48,4 | 45,7 | 0,9 | 40,7 |
| 25 | $C_8$ | $C_4$ | H | 1 | Na | 97,3 | 51,0 | 48,4 | 0,9 | 44,6 |
| 26 | $C_{10}$ | $C_4$ | H | 1 | Na | 88,8 | 41,5 | 39,5 | 3,4 | 35,8 |
| 27 | $C_{12}$ | $C_4$ | H | 1 | Na | 83,7 | 33,0 | 31,4 | 4,1 | 27,5 |
| 28 | $C_6$ | $C_4$ | H | 2 | Na | 98,7 | 57,7 | 54,3 | 0,5 | 51,3 |
| 29 | $C_8$ | $C_4$ | H | 2 | Na | 97,5 | 52,3 | 49,3 | 0,9 | 47,1 |
| 30 | $C_{10}$ | $C_4$ | H | 2 | Na | 95,8 | 55,1 | 51,9 | 1,6 | 48,2 |
| 31 | $C_{12}$ | $C_4$ | H | 2 | Na | 86,9 | 51,3 | 48,1 | 5,2 | 44,3 |
| 32 | $C_{12}$ | $C_4$ | H | 2 | K | 98,7 | 52,7 | 51,3 | 0,5 | 51,7 |
| 33 | $C_{12}$ | $C_4$ | H | 2 | Li | 97,3 | 50,7 | 48,1 | 1,1 | 50,3 |
| 34 | $C_{12}$ | $C_4$ | H | 2 | DEA* | 98,4 | 77,4 | 60,1 | 0,6 | 58,4 |
| 35 | $C_{14}$ | $C_4$ | H | 2 | Na | 85,3 | 36,9 | 34,5 | 4,4 | 32,2 |
| 36 | $C_{16}$ | $C_4$ | H | 2 | Na | 80,9 | 31,8 | 29,7 | 5,1 | 26,5 |
| 37 | $C_6$ | $C_4$ | H | 4 | Na | 96,9 | 62,1 | 60,5 | 1,5 | 60,9 |
| 38 | $C_{14}$ | $C_4$ | H | 4 | Na | 91,5 | 39,1 | 38,1 | 2,8 | 37,2 |
| 39 | $C_6$ | $C_4$ | H | 5 | Na | 96,0 | 51,3 | 48,9 | 1,5 | 45,5 |
| 40 | $C_8$ | $C_4$ | H | 5 | Na | 95,2 | 53,3 | 51,2 | 1,9 | 47,1 |
| 41 | $C_{10}$ | $C_4$ | H | 5 | Na | 81,3 | 55,5 | 53,7 | 8,4 | 44,6 |
| 42 | $C_{12}$ | $C_4$ | H | 5 | Na | 84,1 | 57,0 | 55,3 | 7,6 | 48,3 |
| 43 | $C_{14}$ | $C_4$ | H | 5 | Na | 85,2 | 27,0 | 25,9 | 3,2 | 22,1 |
| 44 | $C_{16}$ | $C_4$ | H | 5 | Na | 89,1 | 48,4 | 46,7 | 4,3 | 42,2 |
| 45 | $C_8$ | $C_4$ | H | 10 | Na | 83,5 | 39,7 | 38,2 | 5,3 | 31,4 |
| 46 | $C_{10}$ | $C_4$ | H | 10 | Na | 78,8 | 38,9 | 37,9 | 7,1 | 30,4 |
| 47 | $C_{12}$ | $C_4$ | H | 10 | Na | 80,8 | 44,7 | 43,7 | 7,5 | 36,6 |
| 48 | $C_{14}$ | $C_4$ | H | 10 | Na | 79,6 | 49,1 | 47,8 | 8,8 | 39,4 |
| 49 | $C_{16}$ | $C_4$ | H | 10 | Na | 76,1 | 45,9 | 44,4 | 9,9 | 35,8 |
| 50 | $C_{10}$ | $C_4$ | H | 15 | Na | 95,5 | 48,1 | 47,2 | 1,9 | 45,2 |
| 51 | $C_{14}$ | $C_4$ | H | 19 | Na | 91,7 | 55,4 | 54,8 | 4,6 | 54,4 |
| 52 | $C_6$ | $C_4$ | H | 27 | Na | 91,9 | 45,7 | 45,1 | 3,7 | 45,1 |
| 53 | $C_{14}$ | $C_4$ | H | 27 | Na | 88,2 | 52,8 | 52,2 | 6,6 | 52,6 |
| 54 | $C_6$ | $C_8$ | H | 2 | Na | 97,0 | 54,6 | 52,5 | 1,3 | 54,9 |
| 55 | $C_{10}$ | $C_8$ | H | 4 | K | 97,5 | 45,4 | 44,5 | 0,9 | 44,4 |
| 56 | $C_{10}$ | $C_8$ | H | 4 | Li | 97,9 | 40,2 | 39,4 | 0,7 | 38,4 |
| 57 | $C_{10}$ | $C_8$ | H | 4 | DEA* | 98,0 | 61,8 | 59,3 | 0,8 | 52,2 |
| 58 | $C_{14}$ | $C_8$ | H | 9 | Na | 94,9 | 50,7 | 49,6 | 2,1 | 44,4 |
| 59 | $C_{10}$ | $C_9$ | $CH_3$ | 10 | Na | 75,3 | 52,2 | 51,2 | 11,3 | 40,1 |
| 60 | $C_{12}$ | $C_9$ | $CH_3$ | 10 | Na | 76,3 | 43,2 | 43,0 | 8,0 | 33,5 |
| 61 | $C_{12}$ | $C_{12}/C_{13}$ | H | 2 | Na | 81,6 | 32,5 | 31,3 | 5,4 | 29,1 |
| 62 | $C_{10}$ | $C_{12}/C_{13}$ | H | 7 | Na | 87,5 | 50,3 | 48,8 | 5,6 | 45,7 |
| 63 | $C_{12}$ | $C_{12}/C_{13}$ | H | 7 | Na | 87,7 | 36,2 | 35,1 | 3,9 | 32,3 |
| 64 | $C_6$ | $C_{12}/C_{14}$ | H | 4 | Na | 92,3 | 66,0 | 64,0 | 4,3 | 62,7 |
| 65[1] | $C_{10}$ | $C_{12}/C_{14}$ | H + $CH_3$ | 2 + 4 | Na | 79,1 | 52,3 | 50,5 | 9,7 | 43,8 |
| 66[2] | $C_{14}$ | $C_{12}/C_{14}$ | H + $CH_3$ | 2 + 4 | Na | 77,8 | 51,4 | 50,2 | 11,1 | 46,3 |
| 67[3] | $C_{12}$ | $C_{12}/C_{14}$ | H + $CH_3$ | 4 + 5 | Na | 79,1 | 54,7 | 52,9 | 9,9 | 43,4 |

TABLE 1-continued

Examples 3-68: Compounds prepared corresponding to general formula (II) ($R^3$ = H)

| Example | $R^1$ | $R^2$ | $R^4$ | n | M | DS % | DR % | AS % | US % | WAS % |
|---|---|---|---|---|---|---|---|---|---|---|
| 68 | $C_{10}$ | $C_{16}/C_{18}$ | H | 11 | Na | 92,5 | 47,1 | 46,3 | 3,2 | 45,0 |

*diethanol amine
[1] A reaction product of 1 mol 1,2-epoxydodecane and 1 mol of the adduct of 2 mol ethylene oxide and 4 mol propylene oxide with 1 mol $C_{12}$–$C_{14}$ fatty alcohol was used in the synthesis.
[2] A reaction product of 1 mol 1,2-epoxyhexadecane and 1 mol of the ethylene oxide/propylene oxide adduct of Example 65 above was used in the synthesis.
[3] A reaction product of 1 mol 1,2-epoxytetradecane and 1 mol of the adduct of 4 mol ethylene oxide and 5 mol propylene oxide with 1 mol $C_{12}$–$C_{14}$ fatty alcohol was used in the synthesis.

Wetting Power

The wetting power of the compounds obtained in accordance with Examples 1 to 68 was determined in accordance with DIN 53 901. The results are shown in Table 2 below.

TABLE 2

Wetting power according to DIN 53 901

| Compound of Example No. | Wetting time (secs) |
|---|---|
| 1 | >300 |
| 2 | 96 |
| 40 | 58 |
| 41 | 17 |
| 42 | 24 |
| 43 | 55 |
| 45 | 100 |
| 46 | 61 |
| 47 | 87 |
| 48 | 130 |
| 49 | 198 |
| 24 | 51 |
| 25 | 38 |
| 26 | 16 |
| 27 | 41 |
| 28 | 66 |
| 29 | 50 |
| 30 | 12 |
| 31 | 23 |
| 35 | 56 |
| 39 | 191 |
| 44 | 132 |
| 3 | 134 |
| 4 | 49 |
| 7 | 166 |
| 8 | 127 |
| 59 | 78 |
| 60 | 115 |
| 62 | 174 |
| 63 | >300 |
| 61 | >300 |

Foaming Power

The foaming power of the compounds of general formula (II) according to the invention was determined in a separate test. In this test, quantities of 100 ml of an aqueous solution of the compounds corresponding to general formula (II) (concentration: 1% by weight AS) were shaken 5 times in a 250 ml graduated standing cylindrical vessel. The foam volume was read off immediately after shaking and then at intervals of 1, 3 and 5 minutes.

Water of 0° Gh and 16° Gh was used for preparing the surfactant solutions.

The results are shown in Table 3 below.

TABLE 3

| Compound of Example No. | Foam volume (ml) | | | | | | | |
|---|---|---|---|---|---|---|---|---|
| | Immediately | | After 1' | | After 3' | | After 5' | |
| | 0° Gh | 16° Gh | 0° Gh | 16° Gh | 0° Gh | 16° Gh | 0° Gh | 16° Gh |
| 1 | 230 | 230 | 180 | 180 | 170 | 170 | 150 | 160 |
| 2 | 210 | 200 | 70 | 120 | 10 | 50 | 8 | 20 |
| 40 | 300 | 300 | 250 | 250 | 250 | 220 | 180 | 180 |
| 41 | 250 | 250 | 180 | 200 | 140 | 170 | 75 | 150 |
| 42 | 250 | 200 | 150 | 140 | 105 | 110 | 40 | 60 |
| 43 | 100 | 120 | 60 | 70 | 30 | 30 | 20 | 20 |
| 45 | 200 | 180 | 145 | 125 | 130 | 120 | 120 | 120 |
| 46 | 200 | 200 | 150 | 150 | 130 | 140 | 70 | 110 |
| 47 | 200 | 200 | 100 | 110 | 10 | 80 | 10 | 40 |
| 48 | 110 | 120 | 10 | 50 | 6 | 25 | 2 | 10 |
| 49 | 90 | 100 | 25 | 45 | 20 | 40 | 20 | 30 |
| 24 | 300 | 300 | 180 | 200 | 140 | 170 | 70 | 160 |
| 25 | 300 | 300 | 250 | 250 | 180 | 200 | 150 | 180 |
| 26 | 300 | 300 | 210 | 210 | 200 | 190 | 180 | 170 |
| 27 | 180 | 160 | 140 | 120 | 120 | 90 | 90 | 70 |
| 28 | 300 | 300 | 250 | 250 | 230 | 230 | 150 | 170 |
| 29 | 300 | 300 | 180 | 250 | 150 | 200 | 50 | 180 |
| 30 | 300 | 300 | 210 | 200 | 210 | 150 | 210 | 100 |
| 31 | 180 | 180 | 130 | 130 | 70 | 100 | 40 | 70 |
| 35 | 120 | 120 | 70 | 70 | 50 | 50 | 50 | 50 |
| 39 | 300 | 250 | 250 | 200 | 200 | 180 | 170 | 150 |
| 44 | 80 | 100 | 30 | 40 | 30 | 30 | 30 | 30 |
| 3 | 300 | 300 | 250 | 250 | 200 | 200 | 190 | 190 |
| 4 | 300 | 300 | 200 | 190 | 160 | 160 | 110 | 100 |
| 7 | 220 | 200 | 170 | 150 | 150 | 130 | 70 | 90 |
| 8 | 140 | 140 | 80 | 70 | 45 | 25 | 25 | 20 |
| 59 | 180 | 150 | 120 | 90 | 100 | 70 | 50 | 50 |
| 60 | 140 | 140 | 90 | 80 | 35 | 40 | 30 | 30 |

TABLE 3-continued

| Compound of Example No. | Foam volume (ml) | | | | | | | |
|---|---|---|---|---|---|---|---|---|
| | Immediately | | After 1' | | After 3' | | After 5' | |
| | 0° Gh | 16° Gh | 0° Gh | 16° Gh | 0° Gh | 16° Gh | 0° Gh | 16° Gh |
| 62 | 140 | 160 | 90 | 110 | 70 | 110 | 50 | 80 |
| 63 | 140 | 140 | 40 | 70 | 30 | 70 | 30 | 50 |
| 61 | 120 | 120 | 60 | 60 | 30 | 50 | 30 | 40 |

Biodegradability

Five of the compounds prepared in accordance with Examples 1 to 68 were tested for their biodegradability by the so-called CB (closed bottle) test which is described in W. K. Fischer, "Zeitschrift Tenside/Detergents" 8, 182 (1971).

The results are shown in Table 4 below.

TABLE 4

| Results of the CB test for biodegradability | |
|---|---|
| Compound of Example no. | BOD$_{30}$/COD (%) |
| 39 | 55 |
| 44 | >60 |
| 60 | >60 |
| 63 | >60 |
| 61 | >60 |

Result

In accordance with the evaluation of the CB test as described in the literature, of the five compounds mentioned, the compound of Example 39 is classified as showing good biodegradability and the compounds of the remaining four Examples as showing very good biodegradability.

Foam Stability Against Soap Load

Foaming properties were tested in accordance with DIN 53902 (foam beating test). In this test foam was produced by beating 200 ml of a solution of the surfactant in a 1 liter cylinder for 30 seconds with a perforated plate fixed to a shaft at a rate of 1 beat per second. The foam volume was measured 30 seconds after the end of the beating.

The measurements were carried out with aqueous solutions containing 2 g/l of the surfactant to be tested. The water hardness was 0° Gh, 11° Gh and 22° Gh, respectively, and again 22° dH in the presence of a soap load in the form of 0.5 g/l sodium oleate.

Test samples were the hydroxy mixed ether sulfates of Examples 3, 7 and 15, a technical sodium salt of an alkyl ether sulfate (AES) obtained by sulfation of an addition product of 1 mole $C_{12}/C_{14}$ fatty alcohol (weight ratio 70:30) with 2 moles ethylene oxide (formula (V): $R^5=C_{12}H_{25}/C_{14}H_{29}$, x=2, A=Na), and mixtures of these components in a weight ratio of 30:70.

The test results are given in Table 5.

TABLE 5

| Surfactant | Foam Stability | | | |
|---|---|---|---|---|
| | Foam Volume (ml) | | | |
| | 0° Gh | 11° Gh | 22° Gh | 22° Gh Na oleate |
| Product of Example 3 | 670 | 590 | 510 | 170 |
| Product of Example 7 | 700 | 580 | 540 | 70 |
| Product of Example 15 | 630 | 550 | 520 | 90 |
| AES | 830 | 840 | 850 | 180 |

TABLE 5-continued

| Surfactant | Foam Stability | | | |
|---|---|---|---|---|
| | Foam Volume (ml) | | | |
| | 0° Gh | 11° Gh | 22° Gh | 22° Gh Na oleate |
| 30% Example 3 + 70% AES | | | | 420 |
| 30% Example 7 + 70% AES | | | | 370 |
| 30% Example 15 + 70% AES | | | | 300 |

We claim:

1. A sulfated hydroxyalkyl polyethylene glycol or hydroxyalkyl polypropylene glycol ether of the formula

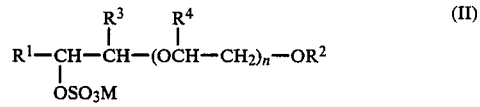

in which

R$^1$ is hydrogen or a linear C$_1$–C$_{16}$ alkyl radical,

R$^2$ is a linear or branched, saturated C$_1$–C$_{22}$ alkyl radical,

R$^3$ is hydrogen or a linear C$_1$–C$_{16}$ alkyl radical,

R$_4$ is hydrogen or a methyl group,

M represents hydrogen, ammonium, alkylammonium, alkanolammonium, in which the alkyl and alkanol radicals each contain from 1 to 4 carbon atoms, or a monovalent metal atom, and n is a number of from 1 to 30.

with the proviso that the total number of carbon atoms in R$^1$ and R$^3$ is between 6 and 16, and mixtures of such compounds.

2. The compound of claim 1 in which R$^1$ is a linear C$_8$–C$_{12}$ alkyl radical and R$^3$ is hydrogen.

3. The compound of claim 1 in which R$^2$ is a linear, saturated C$_1$–C$_{12}$ alkyl radical.

4. The compound of claim 2 in which R$^2$ is a linear, saturated C$_1$–C$_{12}$ alkyl radical.

5. The compound of claim 3 in which R$^2$ is a C$_1$–C$_{12}$ alkyl radical.

6. The compound of claim 4 in which R$^2$ is a C$_1$–C$_{12}$ alkyl radical.

7. The compound of claim 1 in which R$^3$ and R$^4$ are hydrogen.

8. The compound of claim 4 in which R$^3$ and R$^4$ are hydrogen.

9. The compound of claim 6 in which R$^3$ and R$^4$ are hydrogen.

10. The compound of claim 1 in which M is an alkali metal ion, an ammonium group, a C$_1$–C$_2$ mono-, di-, or tri-alkylammonium group, or a C$_2$–C$_3$ mono-, di-, or tri-alkanolammonium group.

11. The compound of claim 4 in which M is an alkali metal ion, an ammonium group, a C$_1$–C$_2$ mono-, di-, or tri-alkylammonium group, or a $C_2$–$C_3$ mono-, di-, or tri-alkanolammonium group.

12. The compound of claim 8 in which M is an alkali metal ion, an ammonium group, a $C_1$–$C_2$ mono-, di-, or tri-alkylammonium group, or a $C_2$–$C_3$ mono-, di-, or tri-alkanolammonium group.

13. The compound of claim 10 in which M is the sodium or potassium ion.

14. The compound of claim 11 in which M is the sodium or potassium ion.

15. The compound of claim 12 in which M is the sodium or potassium ion.

16. The compound of claim 1 in which n is a number of from 1 to 12.

17. The compound of claim 14 in which n is a number of from 1 to 12.

18. A process for the preparation of a sulfated hydroxyalkyl polyethylene glycol or hydroxyalkyl polypropylene glycol ether of the formula

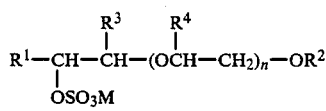

in which $R^1$ is hydrogen or a linear $C_1$–$C_{16}$ alkyl radical, $R^2$ is a linear or branched, saturated $C_1$–$C_{22}$ alkyl radical, $R^3$ is a hydrogen or a linear $C_1$–$C_{16}$ alkyl radical, $R^4$ is hydrogen or a methyl group, M represents hydrogen, ammonium, alkylammonium, alkanolammonium, in which the alkyl and alkanol radicals each contain from 1 to 4 carbon atoms, or a monovalent metal atom, and n is a number of from 0 to 12, with the proviso that the total number of carbon atoms in $R^1$ and $R^3$ is between 6 and 16, and mixtures of such compounds, comprising the steps of A. reacting an epoxide or mixture of epoxides of the formula

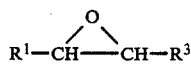

in which $R^1$ and $R^3$ are as defined above, with an alcohol or alcohol alkoxylate, or mixtures thereof, of the formula

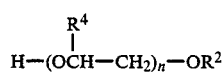

in which $R^2$, $R^4$, and n are as defined above, at an elevated temperature in the presence of a catalyst to form a hydroxyalkyl polyethylene glycol or a hydroxyalkyl polypropylene glycol ether, or mixtures thereof, of the formula

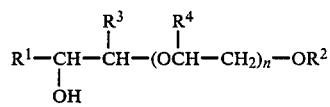

in which $R^1$, $R^2$, $R^3$, $R^4$, and n are as defined above,

B. reacting the compound (I) or mixtures thereof with a sulfating agent to form a crude sulfonation product.

C. contacting the crude sulfonation product with an aqueous, basic solution, and maintaining the resulting mixture at an elevated temperature, D. adjusting the mixture to a pH value in the nuetral or mildly alkaline range, and E. isolating the compound or mixture of compounds of formula (II) from the reaction mixture.

19. The process of claim 18 wherein in step A in the epoxide of formula III $R^1$ is a linear $C_8$–$C_{12}$ alkyl radical and $R^3$ is hydrogen.

20. The process of claim 18 wherein in step A in the alcohol or alcohol alkoxylate of formula IV $R^2$ is a linear, saturated $C_1$–$C_{22}$ alkyl radical.

21. The process of claim 19 wherein in step A in the alcohol or alcohol alkoxylate of formula IV $R^2$ is a linear, saturated $C_1$–$C_{22}$ alkyl radical.

22. The process of claim 18 wherein the step A in the compounds of formula IV $R^2$ is a linear $C_1$–$C_{12}$ alkyl radical, $R^4$ is hydrogen, and n is a number of from 1 to 12.

23. The process of claim 18 wherein in step A the molar ratio of the compounds of formula III to the compounds of formula IV is about 1:1.

24. The process of claim 18 wherein in step A the elevated temperature is in the range of from about 100° to about 180° C.

25. The process of claim 24 wherein the elevated temperature is in the range of from about 120° to about 160° C.

26. The process of claim 18 wherein in step A the catalyst is an alkali metal alcoholate, sulfuric acid, or boron trifluoride etherate, and is used in an amount of from about 0.01 to about 2.0% by weight, based on the total weight of the reaction mixture.

27. The process of claim 26 wherein the catalyst is sodium methylate.

28. The process of claim 18 wherein in step B the sulfating agent is gaseous sulfur trioxide or chlorosulfonic acid.

29. The process of claim 28 wherein the sulfating agent is gaseous sulfur trioxide diluted with air or nitrogen.

30. The process of claim 29 wherein from about 1 to about 10% by volume sulfur trioxide is present in the air or nitrogen.

31. The process of claim 18 wherein in step B the sulfating reaction is carried out at a temperature in the range of from about 10° to about 40° C.

32. The process of claim 19 wherein in step C the aqueous basic solution is a solution of an alkali metal hydroxide, ammonia, a $C_1$–$C_2$ mono-, di-, or tri-alkylamine, or a $C_2$–$C_3$ mono-, di-, or tri-alkanolamine.

33. The process of claim 32 wherein the basic solution is a solution of sodium hydroxide.

34. The process of claim 33 wherein from about 1.0 to about 1.3 mol sodium hydroxide is present per mol of added sulfur trioxide.

35. The process of claim 32 wherein in step C the elevated temperature is in the range of from about 60° to about 100° C.

36. The process of claim 18 wherein in step D the pH adjustment is made with a dilute mineral acid.

37. In a detergent or cleaning composition, the improvement comprising the presence therein of a wetting-effective quantity of the compound of claim 1.

38. In a cosmetic washing or cleaning composition, the improvement comprising the presence therein of a wetting-effective quantity of the compound of claim 1.

39. In a cosmetic washing or cleaning composition, the improvement comprising the presence therein of a wetting-effective quantity of a mixture of
(a) a compound of claim 1, and
(b) a fatty alcohol (polyglycol ether) sulfate of formula (V)

$$R^5-(OCH_2CH_2)_x-OSO_3A \quad (V)$$

in which
$R^5$ is a linear or branched $C_{10}-C_{16}$ alkyl radical,
x is a number of from 0 to 10, and
A represents an ammonium ion, a mono-, di- or tri-alkanolammonium ion having from 2 to 4 carbon atoms in the alkanol radicals, an alkali metal ion, or a magnesium ion equivalent
in a weight ratio of (a):(b) in the range of from about 10:90 to about 90:10.

* * * * *